(12) United States Patent
Bledsoe

(10) Patent No.: US 7,785,283 B1
(45) Date of Patent: Aug. 31, 2010

(54) ANKLE STABILIZING DEVICE

(75) Inventor: Gary Bledsoe, Mansfield, TX (US)

(73) Assignee: Medical Technology, Inc., Grand Prairie, TX (US)

( * ) Notice: Subject to any disclaimer, the term of this patent is extended or adjusted under 35 U.S.C. 154(b) by 14 days.

(21) Appl. No.: 12/177,661

(22) Filed: Jul. 22, 2008

(51) Int. Cl.
*A61F 5/00* (2006.01)
*A61F 5/37* (2006.01)

(52) U.S. Cl. ............................. 602/27; 602/28; 602/29; 602/23; 128/888

(58) Field of Classification Search .................. 602/22, 602/27, 23, 25, 26, 28, 62, 5, 16, 29; 128/888; 128/882; D24/190
See application file for complete search history.

(56) References Cited

U.S. PATENT DOCUMENTS

| | | | |
|---|---|---|---|
| 4,938,777 A | 7/1990 | Mason et al. | |
| RE33,395 E | 10/1990 | Peters | |
| 5,031,607 A | 7/1991 | Peters | |
| 5,067,486 A | 11/1991 | Hely | |
| 5,069,202 A * | 12/1991 | Prock | 602/27 |
| 5,209,722 A * | 5/1993 | Miklaus et al. | 602/27 |
| 5,217,431 A | 6/1993 | Toronto et al. | |
| 5,330,419 A | 7/1994 | Toronto et al. | |
| 5,501,659 A | 3/1996 | Morris et al. | |
| 5,795,316 A | 8/1998 | Gaylord | |
| 5,971,946 A * | 10/1999 | Quinn et al. | 602/27 |
| 6,524,266 B1 | 2/2003 | Peters | |
| 6,656,145 B1 | 12/2003 | Morton | |
| 6,749,578 B2 | 6/2004 | Peters | |
| 6,858,017 B2 * | 2/2005 | Peters | 602/27 |
| 7,128,725 B2 * | 10/2006 | Rabe | 602/27 |
| D550,370 S | 9/2007 | Peters et al. | |
| D552,743 S | 10/2007 | Verkade et al. | |
| D552,744 S | 10/2007 | Verkade et al. | |
| 7,524,295 B1 * | 4/2009 | Peters et al. | 602/5 |
| 2003/0014001 A1 * | 1/2003 | Martin | 602/27 |
| 2006/0084899 A1 * | 4/2006 | Verkade et al. | 602/27 |

* cited by examiner

*Primary Examiner*—Patricia M Bianco
*Assistant Examiner*—Ophelia Hawthorne
(74) *Attorney, Agent, or Firm*—James E. Walton; Richard G. Eldredge

(57) ABSTRACT

A functional ankle brace is custom tailored to optimize the magnitude and direction of the stiffness and fit of the ankle brace, so as to slow down the inverting motion of the ankle joint enough to allow the muscles enough time to act on their own.

19 Claims, 16 Drawing Sheets

ANKLE STABILIZING DEVICE

BACKGROUND OF THE INVENTION

1. Field of the Invention

The present application relates to ankle braces. In particular, the present application relates to ankle braces that restrain the ankle and adjacent appendages.

2. Description of Related Art

The human ankle joint, medically known as the talocrural joint, is formed by three bones: the tibia, the fibula, and the talus. These bones are connected to themselves and to the other bones of the foot by ligaments. The ligaments, which are formed from tough bands of elastic tissue, help define and restrict the rotational movement of the foot relative to the leg. The ligaments of the ankle joint are grouped into two categories: (1) the lateral collateral ligaments, and (2) the medial collateral ligaments.

The lateral collateral ligaments include the anterior talofibular ligament (ATFL), calcaneofibular ligament, the talocalcaneal ligament, the posterior talocalcaneal ligament, and the posterior talofibular ligament (PTFL). The ATFL passes from the tip of the lateral malleolus to the talus anteriorly, and functions to limit plantar flexion of the joint. The calcaneofibular ligament passes from the lateral malleolus to the calcaneus, with the talocalcaneal ligament running at its base. The calcaneofibular ligament and the talocalcaneal ligament resist adduction. The PTFL passes from the tip of the lateral malleolus to the talus posteriorly. The posterior talocalcaneal extends this band to the calcaneus. The PTFL and the posterior talocalcaneal ligament both limit dorsiflexion.

The medial collateral ligaments, or deltoid ligament complex, include the tibionavicular ligament, the calcaneotibial ligament, the anterior talotibial ligament, and the posterior talotibial ligament. The tibionavicular ligament runs anteriorly form the medial malleolus to the navicular bone. The calcaneotibial ligament runs from the tip of the medial malleolus to the edge of the calcaneus. The tibionavicular ligament and the calcaneotibial ligament prevent abduction. The anterior and posterior talotibial ligaments run anteriorly and posteriorly between the medial malleolus and the talus. The anterior and posterior talotibial ligaments limit plantar flexion and dorsiflexion respectively.

The ATFL and the PTFL connect the bottoms of the tibia and fibula. The interosseous ligament spans the length of the tibia and fibula. The ATFL, the PTFL, and the interosseous ligament make up what is known as the syndesmotic ligament complex. The syndesmotic ligament cooperates with the ankle joints to allow the ankle to articulate.

A large portion of these ligaments is made up of collagenous fibers. During initial growth, collagenous fibers form in a web-like arrangement, due to the tension exerted by corresponding bones. The web-like arrangement supplies both elasticity and tensile strength to the ligaments. When a ligament is forced to stretch beyond its normal range, a sprain occurs. Ankle sprains are commonly categorized into three grades: Grade 1, characterized by slight stretching and some damage to the fibers (fibrils) of the ligament; Grade 2, characterized by partial tearing of the ligament, resulting in abnormal looseness (laxity) of the ankle joint; and Grade 3, characterized by complete tearing of the ligament, in which gross instability occurs.

Among these grades of ankle sprains, the two most common types are: (1) sprains to either the lateral ligaments or the medial ligaments of the ankle, which are referred to as "normal" ankle sprains; and (2) sprains to the syndesmotic ligament complex, which are known as "high" ankle sprains. Normal ankle sprains account for the vast majority of ankle sprains, occurring during the performance of ordinary activities. About 90% of normal ankle sprains are to the lateral ligaments, and about 10% of normal ankle sprains are to the medial ligaments. A person can sprain the lateral or medial ligaments of the ankle without affecting the syndesmotic ligaments. On the other hand, high ankle sprains are usually caused by injury or tearing of the syndesmotic ligaments. Most high ankle sprains are suffered by athletes undergoing extremely strenuous activity.

Sprained ankles can be healed; however, the healing process can take several weeks or months, depending upon the method of treatment and rehabilitation. Although most doctors recommend the well-known RICE treatment, i.e., rest, ice, compression, and elevation for the time period immediately after the ankle sprain, there are many methods of rehabilitating ankle sprains. For example, casts, wraps, and tape are often used to restrain and immobilize the ankle, so that the ligaments may heal through the reformation of the collagenous fibers. However, when the ankle is immobilized, there is a risk that the collagenous fibers will reform in a skewed arrangement due to a lack of tension on the ligaments. When ligaments reform with a skewed arrangement, they have decreased elasticity and tensile strength. As a result, subsequent conditioning must be undergone to resolve the skewed arrangement of the collagenous fibers and to regain the original elasticity and tensile strength of the ligament. Unfortunately, even after conditioning, ligaments that have been reformed with skewed growth of the collagenous fibers rarely obtain their original elasticity and tensile strength, because the collagenous fibers cannot fully rearrange themselves into the original web-like formation.

For high ankle sprains, while control of the exertion of the syndesmotic ligament is necessary, complete restraint of the ankle joint is not desirable. Because it is generally undesirable to completely immobilize the ankle during healing, ankle braces that allow for slight mobility of the ankle during the rehabilitation process are commonly prescribed.

Generally, ankle braces may be classified as one of three types: (1) ankle wraps; (2) ankle supports; and (3) functional ankle braces. Unfortunately, with current ankle braces, there is a trade-off between comfort and support. Ankle wraps are normally made of a neoprene material that surrounds the ankle. The problem with ankle wraps is that although they provide compression and warmth, i.e., comfort, they provide little or no stiffness, i.e., support.

Ankle supports usually consist of two stirrups and reinforcing elements that are secured along the sides of the ankle. These ankle supports compress the fibula and tibia toward each other in an attempt to allow the syndesmotic ligaments to heal. However, because the fibula extends slightly below the tibia, when the ankle rolls, shear is transferred to the fibula, thereby rendering the ankle support inadequate. Some ankle supports are multi-piece devices held together with straps or laces. These lace-up devices are difficult to administer and do not provide adequate stiffness.

Functional ankle braces typically consists of soft members that are connected to rigid frames. The rigid frames are multi-piece assemblies that are held together with flexible adjustment straps. These functional ankle braces compress the bones of the ankle toward one another, and constrain movement of the ankle relative to the leg. Unfortunately, although the soft members can adapt somewhat to the contours of the ankle, the stiff frames do not fit well, primarily because the frame members are rigid and the connecting straps are flexible. When the stiff frames are tightened around a movable joint, such as the ankle, the user experiences discomfort.

Other problems are that the stiff frames, which are often made of aluminum, cannot be formed in the field, and are too hard to get fitted properly. More importantly, these types of ankle braces are not shaped, configured, or designed to properly account for the anatomy and degree of bending between the ankle and leg. In addition, the adjustment straps on conventional functional ankle braces pose many problems, for example, they require two hands to fasten them about the rigid frames, the tension changes each time they are fasten and unfastened, and they are located at places that cause discomfort, for example, around the Achilles tendon. This makes them difficult to administer, particularly when the braces are applied and taken off repeatedly.

Although great strides have been made in the area of treating ankle sprains, many shortcomings remain.

BRIEF DESCRIPTION OF THE DRAWINGS

The novel features believed to be characteristic of the application are set forth in the appended claims. However, the application itself, as well as a preferred mode of use and further objectives and advantages thereof, will best be understood by reference to the following detailed description when read in conjunction with the accompanying drawings, wherein:

DESCRIPTION OF THE DRAWINGS

The present application represents the discovery that a functional ankle brace can be custom tailored to optimize the magnitude and direction of the stiffness and fit of the ankle brace, so as to slow down the inverting motion of the ankle joint enough to allow the muscles enough time to act on their own.

Figure 1:
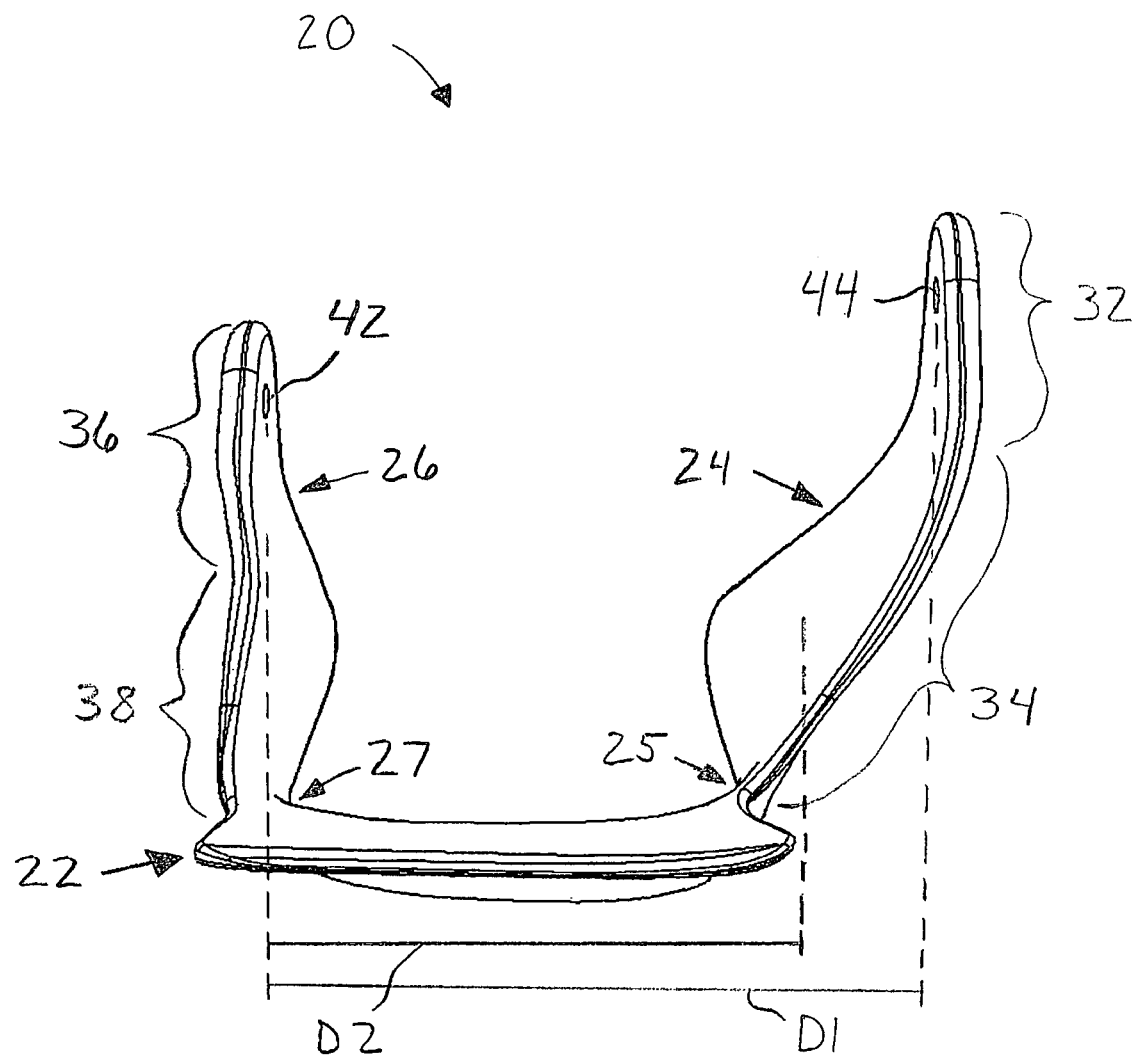
FIG. 1 is a front view of a right foot plate of an ankle brace according to the preferred embodiment of the present application.

Referring to FIG. 1, there is shown a front view of a right foot plate 20 of an ankle brace 10 (see FIG. 6) according to the preferred embodiment of the present application. Foot plate 20 is asymmetric, having a base portion 22, a lateral-upright portion 26, and a medial-upright portion 24. Base portion 22 includes a lateral edge 27 opposing a medial edge 25. Lateral-upright portion 26 and medial-upright portion 24 upwardly extend from both lateral edge 27 and medial edge 25, respectively. In the preferred embodiment, lateral edge 27 and medial edge 25 are curved edges. In an alternative embodiment, asymmetric foot plate 20 is formed according to the contours of a user's foot and ankle.

Medial-upright portion 24 has an upper portion 32 and a lower portion 34. Lateral-upright portion 26 has an upper portion 36 and a lower portion 38. Upper portions 32 and 36 are separated by a distance D1. Lower portions 34 and 38, are separated by a distance D2, where D1 is preferably greater than D2. Medial-upright portion 24 narrows in width and increases in thickness toward pivot point 44. Lateral-upright portion 26 narrows in width and increases in thickness toward pivot point 42.

Figure 2:
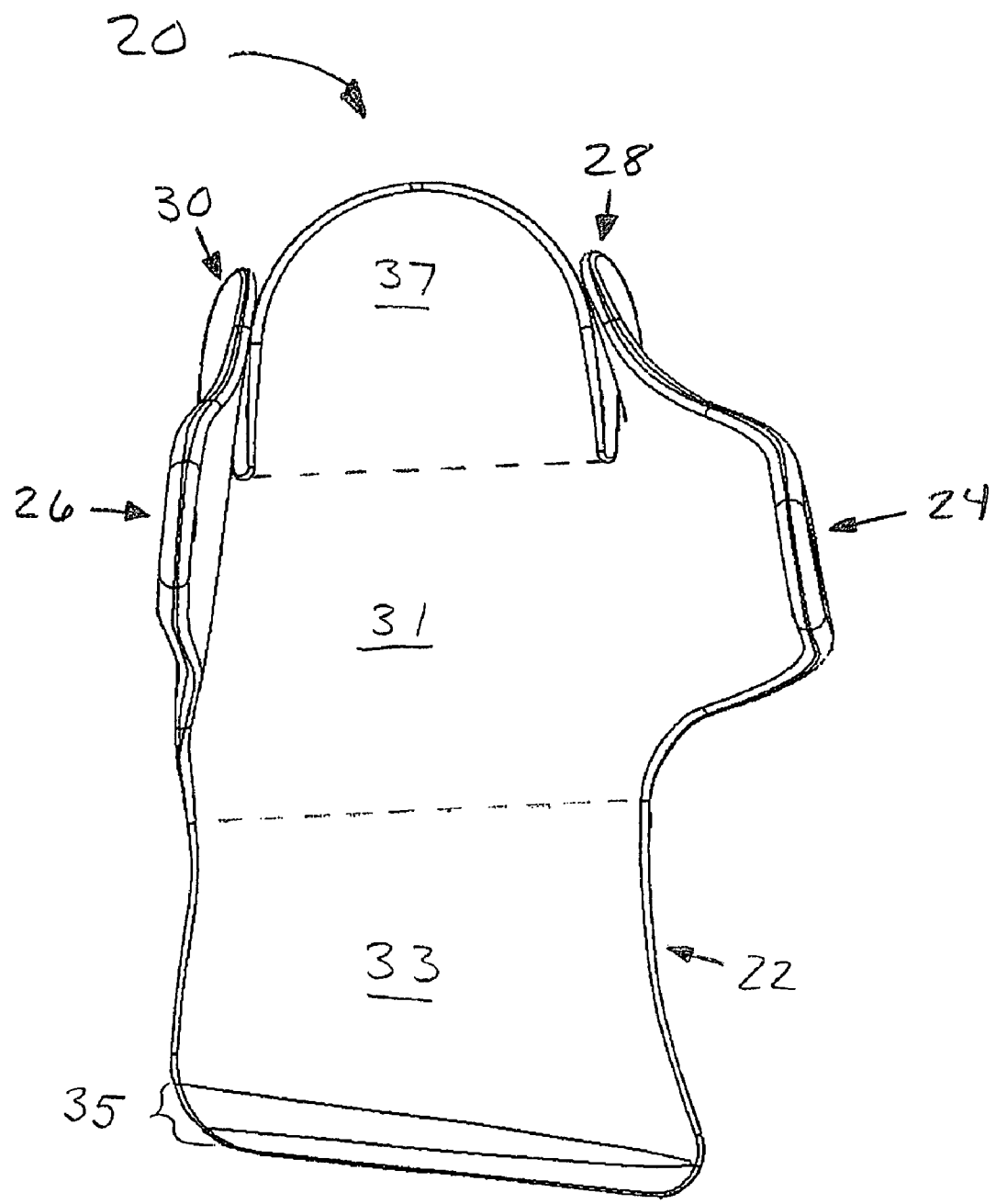
FIG. 2 is a top view of a right foot plate of FIG. 1.

Referring now also to FIG. 2 in the drawings, right foot plate 20 is shown in a top view. Lateral-upright portion 26 and medial-upright portion 24 are preferably anatomically contoured to conform to the user's maelloli. Lateral-upright portion 26 includes a rearwardly-extending tab portion 30 positioned above lateral edge 27. Medial-upright portion 24 includes a rearwardly-extending tab portion 28 positioned above medial edge 25.

Base portion 22 has a front portion 33, an arch portion 31, and a rear portion 37. Front portion 33 preferably includes a tapered front edge 35. In the preferred embodiment, base portion 22 increases in width from arch portion 31 to tapered front edge 35. Rearwardly-extending tab portions 28 and 30 extend to substantially similar lengths from medial-upright portion 24 and lateral-upright portion 26, respectively.

Front portion 33 widens to accommodate the shape of the metatarsus, but stops extending along an axis which corresponds to the juncture of the metatarsal and the phalangeal region of the foot. The thickness of upper portions 36 and 32 along with the rivets (not illustrated) which extend through pivot points 44 and 42 assist to prevent rolling of the ATFL, the PTFL, and the interroseous ligament. The shape of asymmetric foot plate 20 allows for movement of the phalanges and the Achilles tendon, while providing for control of the ankle stabilizing device 10. By allowing the Achilles tendon and the phalanges to move, the ATFL, PTFL, and interoseous ligament are allowed to pull in tension and provide a web-like reformation of the collagen fibers. The bottom portion of asymmetric foot plate 20 is slightly curved along lateral edge 27 and medial edge 25 to account for the transition from lateral-upright portion 26 to medial-upright portion 24.

Figure 3:
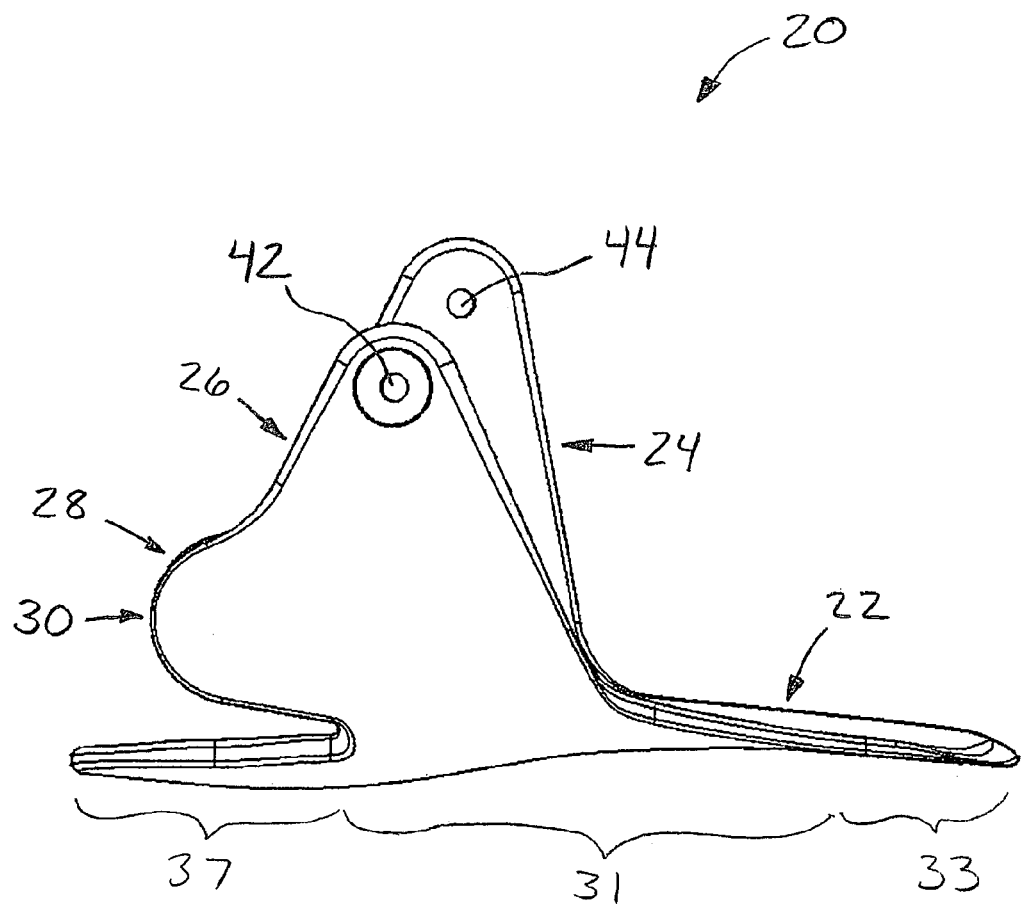
FIG. 3 is a left side view of the right foot plate of FIG. 1.

Referring now also to FIG. 3 in the drawings, right foot plate 20 is shown in a left side view. Arch portion 31 provides an arcuate transition between front portion 33 and rear portion 37 to account for the natural arch of the calcaneal and metatarsal region of the foot. Base portion 22 is shaped to accommodate the contours of a shoe and a foot, as front portion 33 downwardly slopes and corresponds to the curvature of the bottom of the calcaneus and metatarsus. Front portion 33 is not as thick as rear portion 37, in order to constrain flexing to the phalangeal region of the foot.

Rear portion 37 provides an upward concave extending rearwardly from arch portion 31, and extends further than rearwardly-extending tab portions 28 and 30. Medial-upright portion 24 extends further from base portion 22 than lateral-upright portion 26. Accordingly, pivot point 44 is located further from base portion 22 than pivot point 42.

Figure 4:
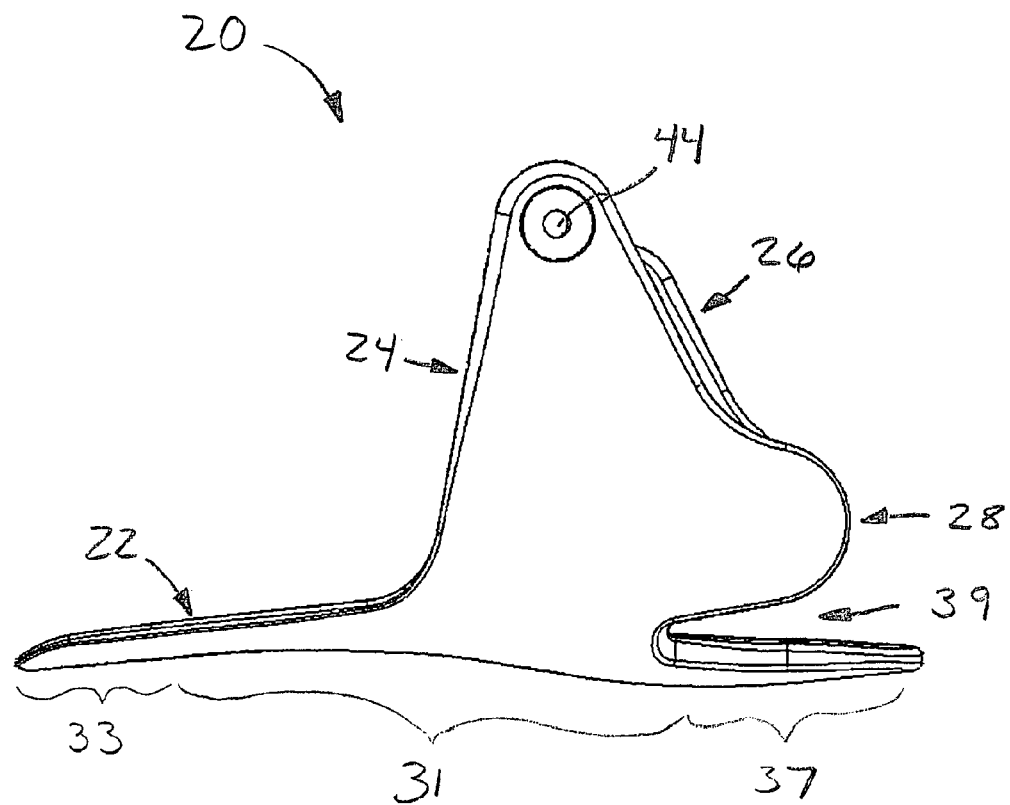
FIG. 4 is a right side view of the right foot plate of FIG. 1.

Referring now also to FIG. 4, right foot plate 20 is shown in a right side view. Rearwardly extending tab members 28 and 30 of medial and lateral-upright portions and 26 both curve inwardly in a rounded fashion to accommodate curvature the calcaneus along with the posterior of the foot. Additionally, there is a gap 39 between rearwardly extending tab member 28 and rear portion 37, as well as rearwardly extending tab member 30 and rear portion 37, which provides flexibility to rear portion 37. Rear portion 37 provides heel support which fits a shoe and the foot better while providing increased support of the arch and midfoot.

Figure 5:
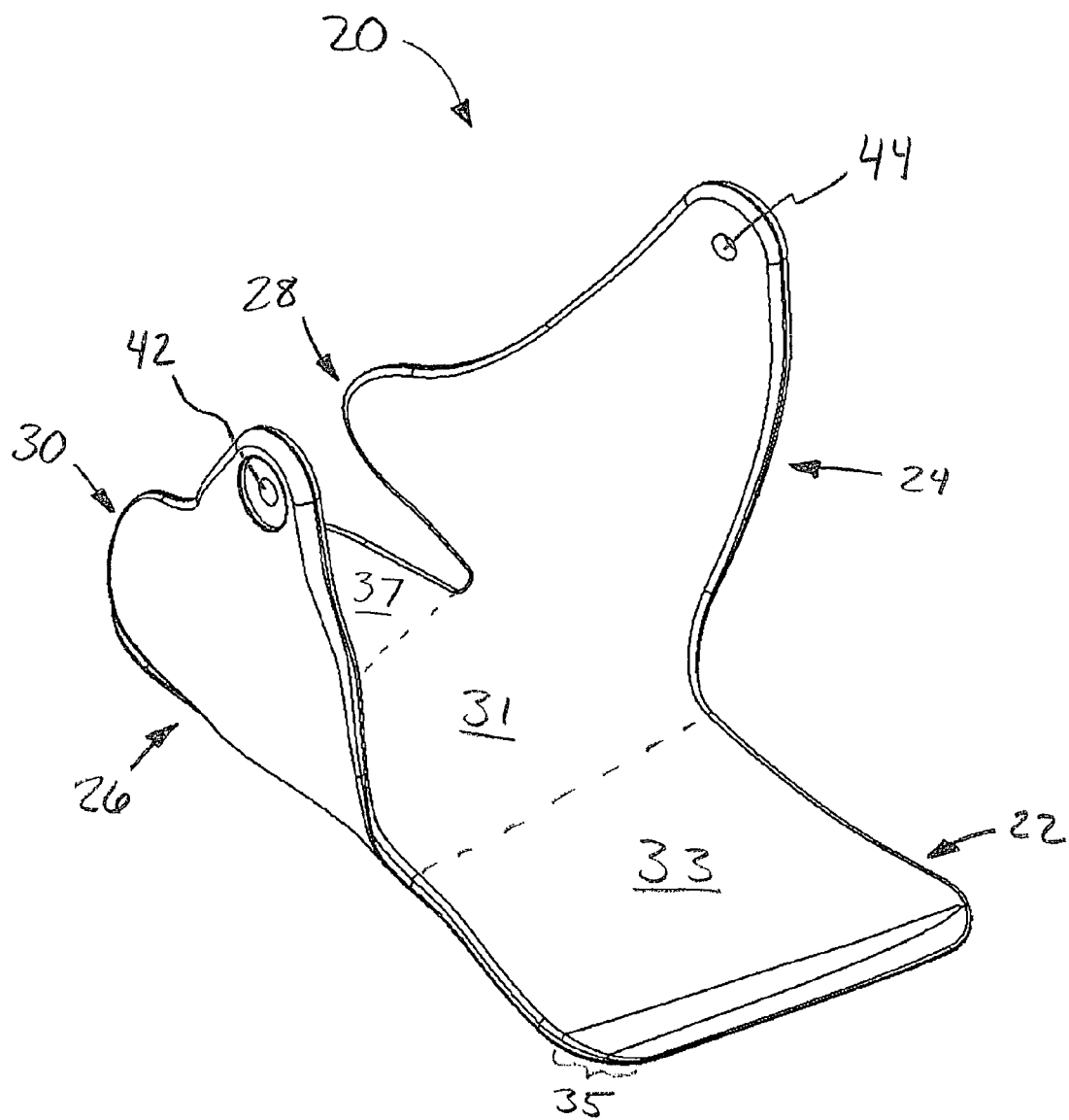
FIG. 5 is a perspective view of the right foot plate of FIG. 1.

Referring now also to FIG. 5 in the drawings, right foot plate 20 is shown in a perspective view. Medial-upright portion 24 curves to accommodate the medial malleolus as it extends to meet to medial leg member 50 via pivot point 42. Similarly, lateral-upright portion 26 is shaped to accommodate the lateral malleolus as it extends to meet lateral leg member 60 via pivot point 44. Medial-upright portion 24 and lateral-upright portion 26 are formed according to the shape of the sides of the calcaneus and provide space at the rear, to allow room for the heel and Achilles tendon to articulate.

Figure 6:
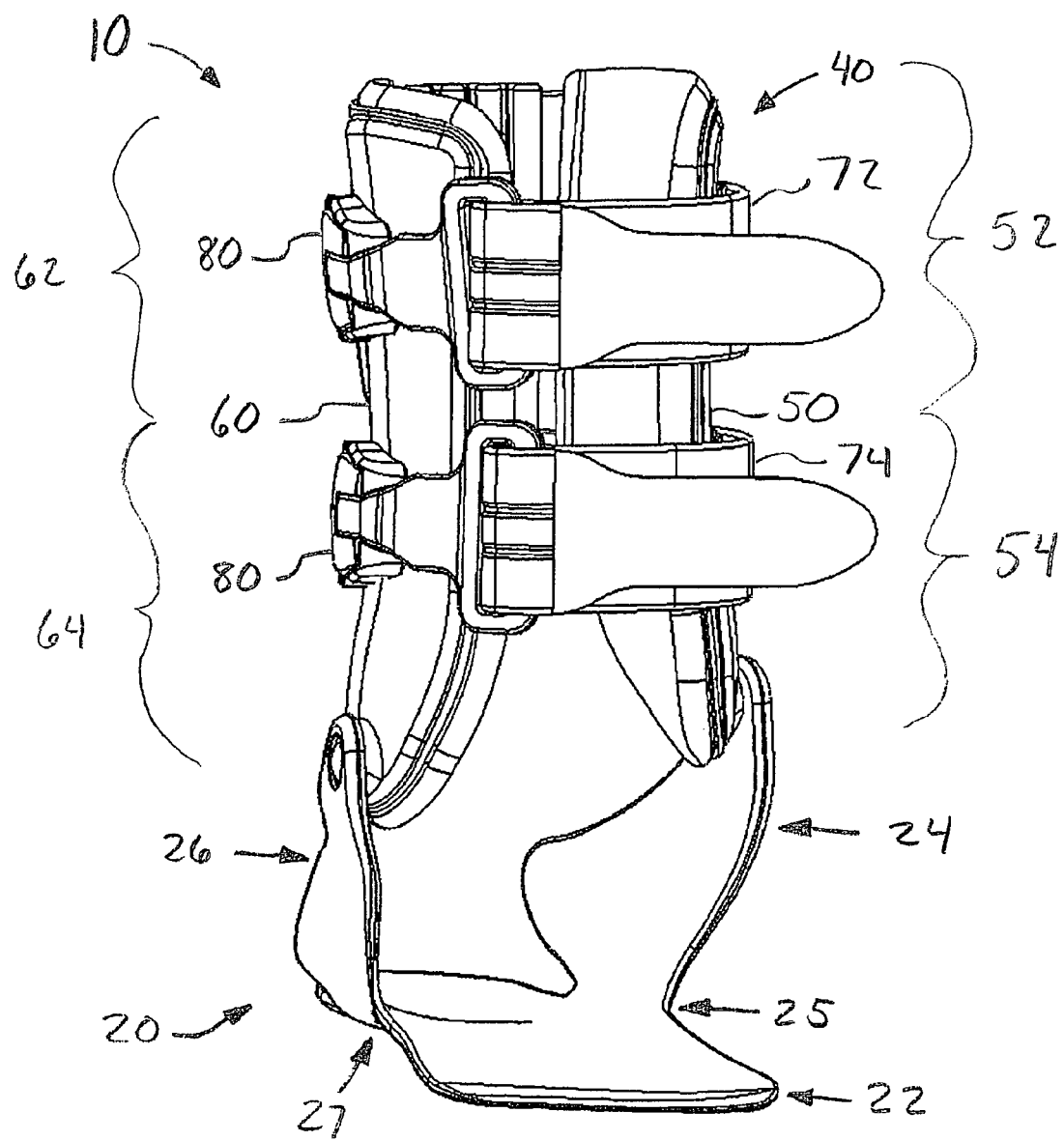
FIG. 6 is a perspective view of a right ankle brace according to the preferred embodiment of the present application.

Referring now also to FIG. 6 in the drawings, ankle brace 10 is shown in a perspective view. By making larger ankle braces thicker, the ankle braces come closer to balancing the stiffness of the ankle brace with a user's body weight. Thus, a large-size ankle brace is thicker than a medium-size ankle brace, or a small-size ankle brace. This balancing of the stiffness and selection of the proper alloy slows down the movement of an ankle into inversion or eversion, where excessive strain would be placed on healing ligaments, or in prophylactic use where stress would be placed on the good ligaments. Advantageously, slowing down these abnormal movements allows time for the muscles to contract and reach sufficient contractile force to prevent further loading of the ligaments, thereby preventing a spraining of the ankle and protecting already injured ligaments from further damage, in all but the most extreme maneuvers.

Asymmetric foot plate 20 and a leg assembly 40, make up ankle stabilizing device 10. Base portion 22 preferably includes a lateral edge 27 and an opposing medial edge 25. A lateral-upright portion 26 extends up from the lateral edge 27 and a medial-upright portion 24 extends up from the medial edge 25. Leg assembly 40 is pivotally engaged to lateral-upright portion 26 and medial-upright portion 24. In one exemplary embodiment, a rivet pivotally engages leg assembly 40 to foot plate 20. Medial-upright portion 24 extends farther than lateral-upright portion 26. Leg assembly 40 is made up of a medial leg member 50 and a lateral leg member 60. Medial leg member 50 and lateral leg member 60 pivotally engages the asymmetric foot plate 20

Figure 7:
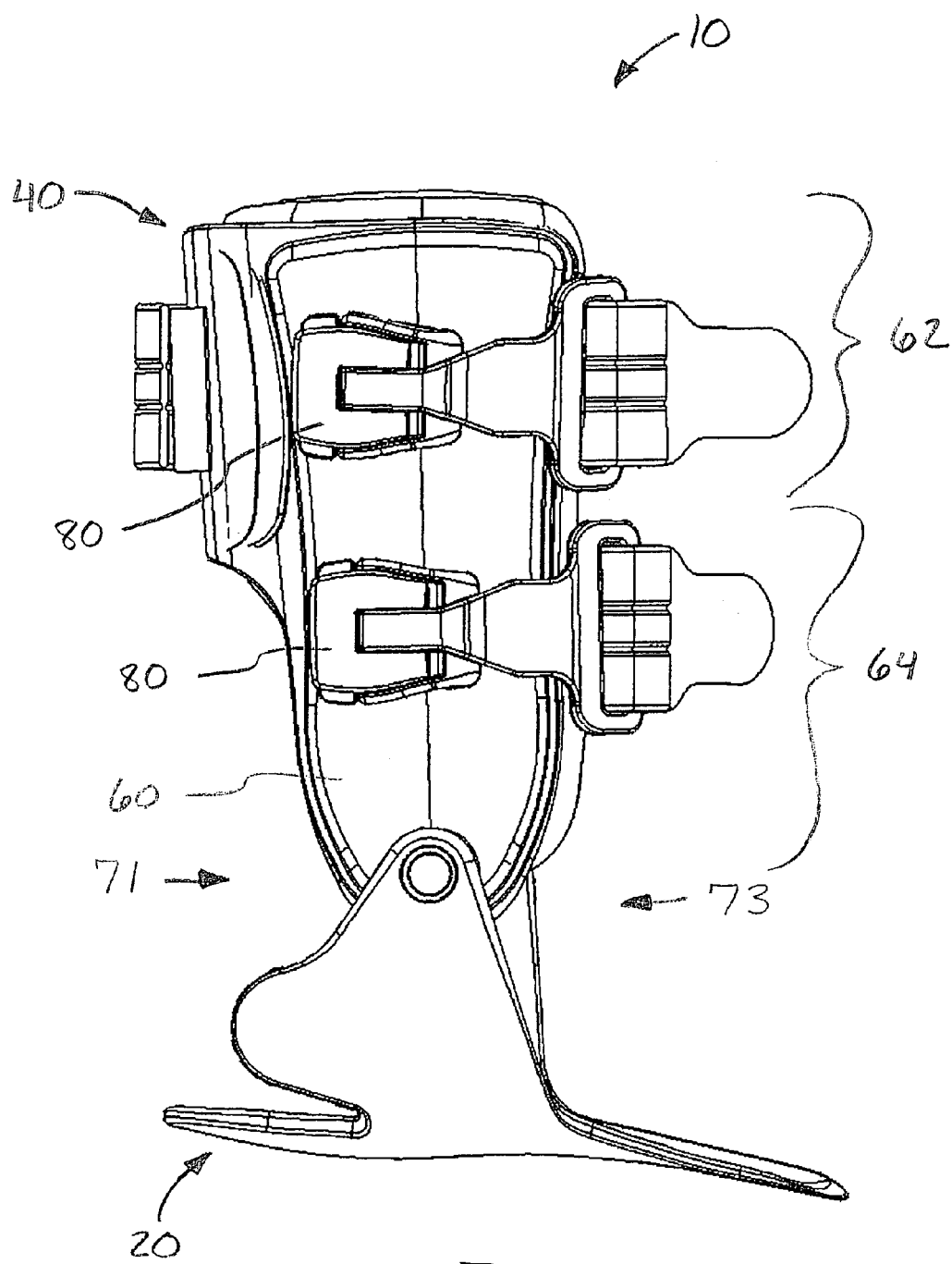
FIG. 7 is a left side view of the ankle brace of FIG. 6.

Referring now also to FIG. 7 in the drawings, ankle brace 10 is shown in a right side view. Ankle stabilizing device 10 preferably includes a posterior void 71 and an anterior void 73. A first strap member 72 securely couples upper medial portion 44 and upper lateral portion 62 around a wearer's leg. A second strap member 74 securely couples the lower medial portion 54 and the lower lateral portion 64 around a wearer's leg. At least one single pin quick release member 80 is connected to lateral leg member 60 in order to couple first strap member 72 or second strap member 74. In an alternative embodiment, at least one single pin quick release member 80 is connected medial leg member 50 in order to couple first strap member 72 or second strap member 74. Both lower medial and lateral portions 54 and 64 preferably extend outwardly to accommodate a wearer's malleoli. In the preferred embodiment, both lower medial and lateral portions 54 and 64 are thicker than upper medial and lateral portions 52 and 62 for the purpose of stabilizing a wearer's malleoli. By having first strap member 72 and second strap member 74 couple both upper medial and lateral portions 52 and 62 and both lower medial and lateral portions 54 and 64 via the anterior void 73, articulation of the Achilles tendon is allowed through posterior void 71. Second strap member 74 and first strap member 72 connect to medial leg member 50 and lateral leg member 60 using a single pin quick release member 80 and hook and pile material.

Figure 8:
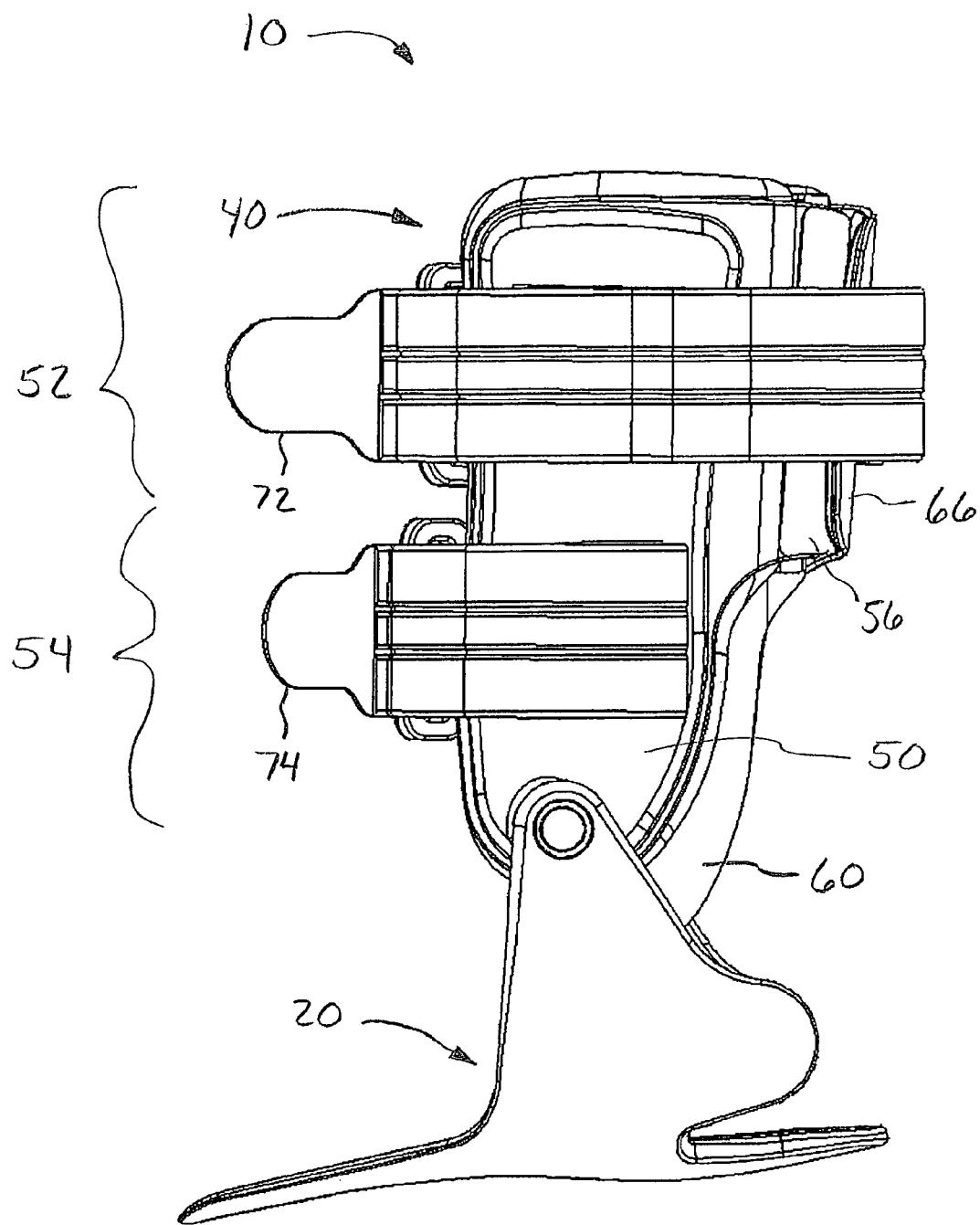
FIG. 8 is a right side view of the ankle brace of FIG. 6.

Referring now also to FIG. 8 in the drawings, ankle brace 10 is shown in a left side view. Medial leg member 50 and lateral leg member 60 are preferably non-planar and may adapt to the curvature of a wearer's leg and ankle. Medial leg member 50 includes an upper portion 52 and a lower portion 54, while lateral leg member 60 includes an upper portion 62 and a lower portion 64. Medial leg member 50 and lateral leg member 60 conform to the shape of the soleus muscle as they transition from upper portions 24 and 26 to lower portions 25 and 27. Medial leg member 50 and lateral leg member 60 attach to one another about rear portions 31 and 33 to account for the shape of the soleus muscle. The lower portions 25 and 27 of medial leg member 50 and lateral leg member 60 align with and couple to medial-upright portion 24 and lateral-upright portion 26. Medial leg member 50 and lateral leg member 60 couple about the front of ankle stabilizing device 10 via second strap member 74 and first strap member 72.

Medial leg member 50 has a lower medial portion 54, an upper medial portion 54, and a rearwardly extending medial flange 56 which extends from the upper medial portion 54. Lateral leg member 60 preferably includes a lower lateral portion 64, an upper lateral portion 62, and a rearwardly extending lateral flange 66 which extends from the upper lateral portion 62. Both the rearwardly extending lateral flange 66 and the rearwardly extending medial flange 56 can curve to tangentially mate each other. Rearwardly extending lateral flange 66 can be removably coupled to rearwardly extending medial flange 56.

Figure 9:
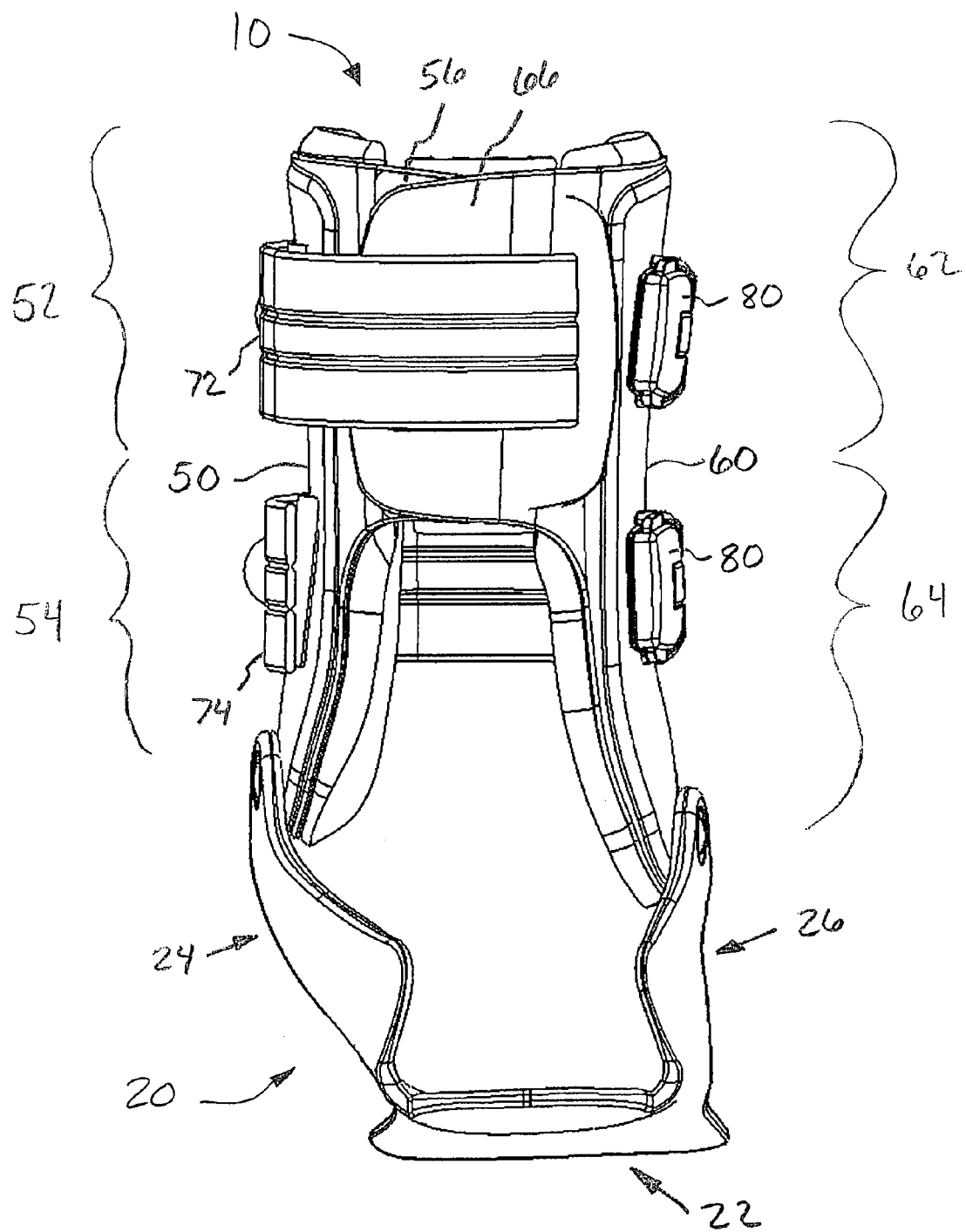
FIG. 9 is a rear view of the ankle brace of FIG. 6.

Referring now also to FIG. 9 in the drawings, ankle brace 10 is shown in a rear view. Asymmetric foot plate 20, medial leg member 50, and lateral leg member 60 conform to the shape of the foot and the ankle. Asymmetric foot plate 20 conforms to the shape of tarsal and metatarsal bones. Medial leg member 50 and lateral leg member 60 attach to medial-upright portion 24 and lateral-upright portion 26 via pivot points 44 and 42.

Pivot points 44 and 42 provide articulation to medial leg member 50 and lateral leg member 60 about asymmetric foot plate 20. Asymmetric foot plate 20, medial leg member 50, and lateral leg member 60 adapt to the natural position of the lateral malleolus and the medial malleolus. Since the lateral malleolus extends slightly below the medial malleolus, medial-upright portion 24 and lateral-upright portion 26 extend to different heights from asymmetric foot plate 20. Thus, pivot points 44 and 42 are positioned on medial-upright portion 24 and lateral-upright portion 26 to account for the articulation of the lateral and medial malleolus. Accordingly, medial leg member 50 and lateral leg member 60 are offset from one another due to the location of pivot points 44 and 42. Single pin quick release members 80 attach to lateral leg member 60 while second strap member 74 and first strap member 72 attach to medial leg member 50. Single pin quick release members 80 are allowed to swivel about the surface of lateral leg member 60. Single pin quick release members 80 align generally parallel to one another and secure second strap member 74 and first strap member 72.

Figure 10:
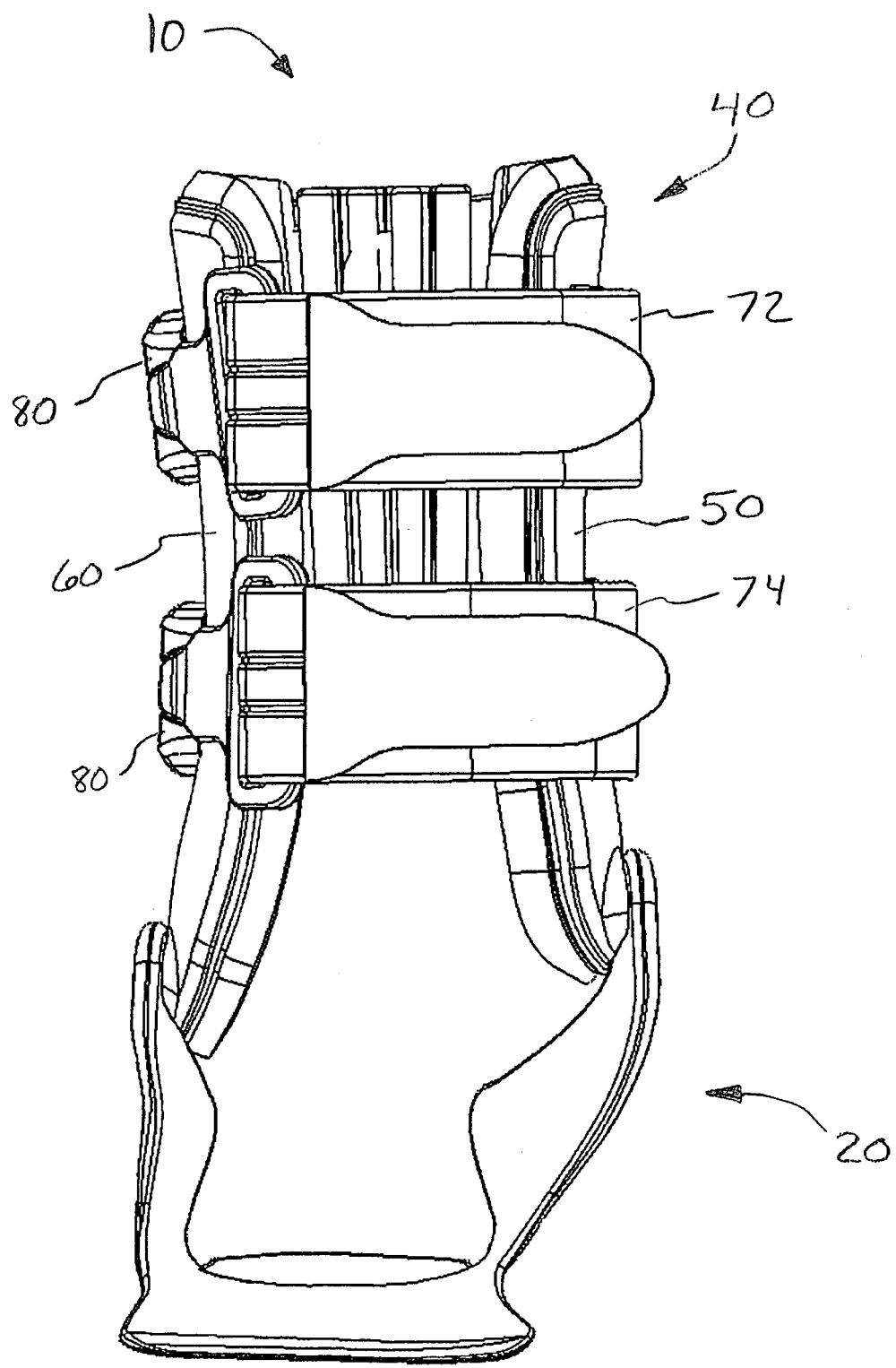
FIG. 10 is a front view of the ankle brace of FIG. 6.

Referring now also to FIG. 10 in the drawings, ankle brace 10 is shown in a front view. Single pin quick release members 80 allow for quick fastening and removal of second strap member 74 and first strap member 72. Second strap member 74 and first strap member 72 secure to medial leg member 50 and lateral leg member 60 and are made of a substantially non-elastomeric hook and pile material. Second strap member 74 and first strap member 72 can attach to medial leg member 50 and lateral leg member 60 in a releasable manner, e.g., via single pin quick release members 80 and hook and pile fasteners. Additionally, second strap member 74 and first strap member 72 can attach to medial leg member 50 and lateral leg member 60 in a permanent manner, e.g., via sewing.

Single pin quick release members 80 may be located on both medial leg member 50 and lateral leg member 60 for attaching first strap member 72 and second strap member 74. Alternatively, hook and pile material may be located on both medial leg member 50 and lateral leg member 60 to attach first strap member 72 and half strap member 80.

In operation, single pin quick release members 80, along with second strap member 74, and first strap member 72 operate via self securing means and hook and pile connections (not shown). Second strap member 74 and first strap member 72 employ hook and pile connections to secure to medial leg member 50 and lateral leg member 60. One end of both second strap member 74 and first strap member 72 secure to the hook and pile connections of medial leg member 50 and lateral leg member 60. Opposing ends of second strap member 74 and first strap member 72 attach to single pin quick release members 80 and to opposite sides of second strap member 74 and first strap member 72.

Figure 11:
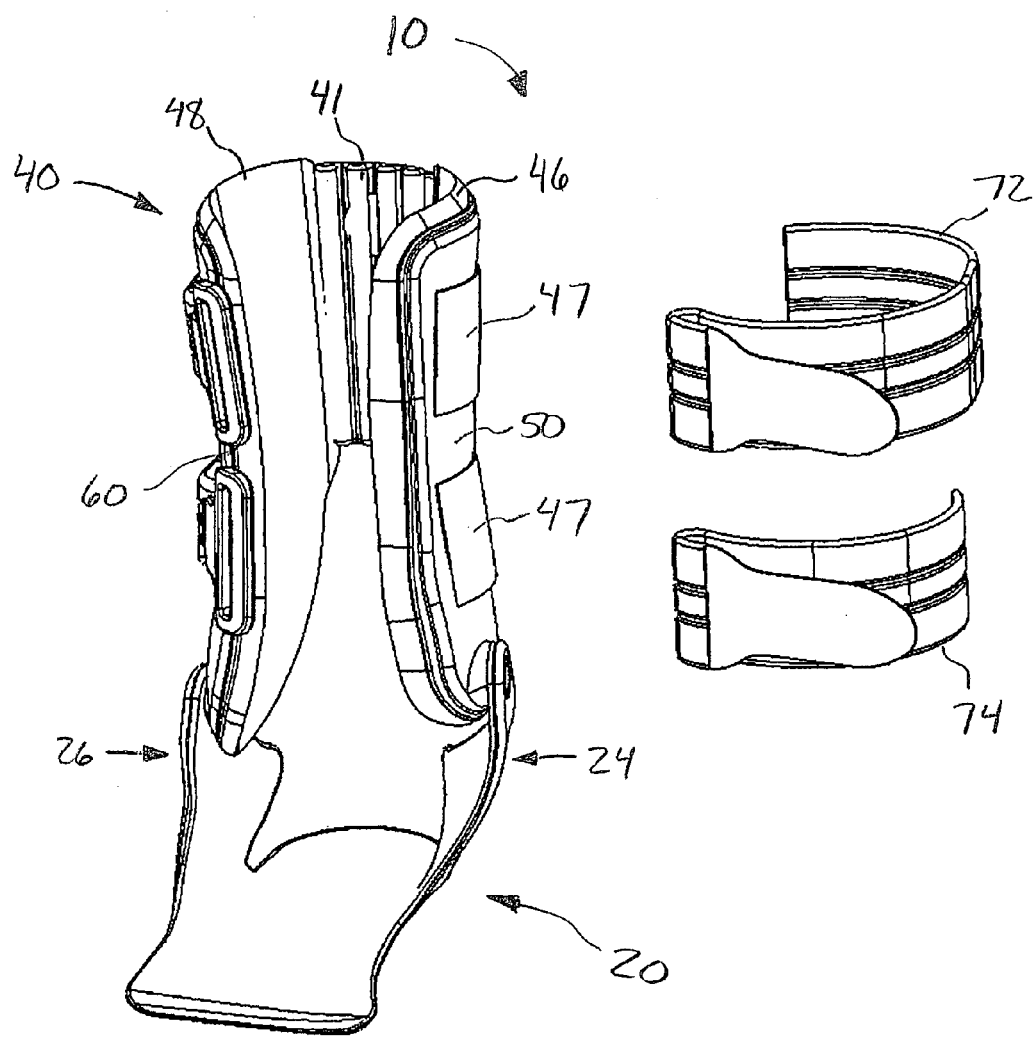
FIG. 11 is a partially exploded view of the ankle brace of FIG. 6.

Referring now also to FIG. 11 in the drawings, ankle brace 10 is shown in a partially exploded view. Tibular pad 46 and fibular pad 48 attach to medial leg member 50 and lateral leg member 60 to protect the lower leg. Rear pad 41 attaches rearwardly extending medial and lateral flanges 56 and 66 of medial leg member 50 and lateral leg member 60 via hook and pile adaptations 43. Hook and pile pads 47 affix to the outer perimeter of medial leg member 50 for attaching second strap member 74 and first strap member 72.

Figure 12:
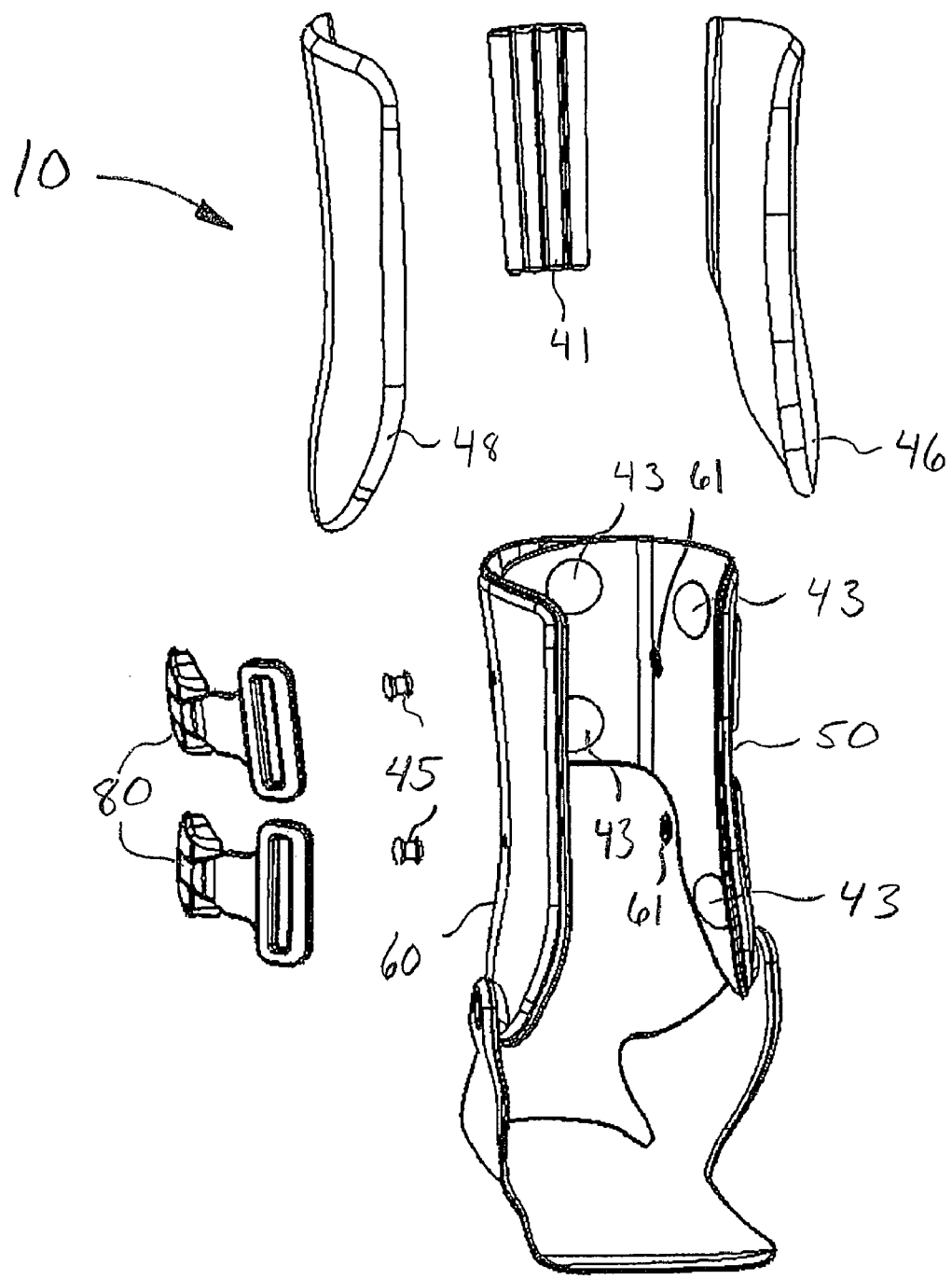
FIG. 12 is an exploded view of the ankle brace of FIG. 6.

Referring now also to FIG. 12 in the drawings, ankle brace 10 is shown in an exploded view. Tibular pad 46 is fashioned according to the shape of a tibia and medial leg member 50 while fibular pad 48 is fashioned according to the shape of a fibula and lateral leg member 60. Similarly, single pin quick release members 80 fasten to lateral leg member 60 via rivets 45 and washers 61. In alternative embodiments, single pin quick release members 80 may fasten to medial leg member 50 via rivets 45. Tibular pad 46, fibular pad 48, and rear pad 41 are preferably made of hook and pile material. Hook and pile adaptations 43 affix to both the interiors of medial leg member 50 and lateral leg member 60 for attaching tibular pad 46, fibular pad 48, and rear pad 41. Rear pad 41 is made from four tube shaped air pockets that extend along the rearwardly extending medial and lateral flanges 56 and 66 and attach medial leg member 50 and lateral leg member 60. Each of the tube shaped air pockets are surrounded by hook and pile material. Each of the tube shaped air pockets may be severed from one another by cutting and may individually attach to medial leg member 50 and lateral leg member 60. In alternative embodiments, any number of tube shaped air pockets may be employed. For example, in the event that a wearer has a large soleus, the rear pad 41 may be made of eight tube shaped air pockets.

First strap member 72 wraps from upper portion 52, around medial leg member 50, and secures to lateral leg member 60 via a single pin quick release member 80. Second strap member 74 wraps from medial leg member 50 and secures to lateral leg member 60 via a single pin quick release member 80. Second strap member 74 acts to relieve stress exerted on the Achilles tendon while providing for increased control of and support to the upper and lower ankle.

Figure 13:
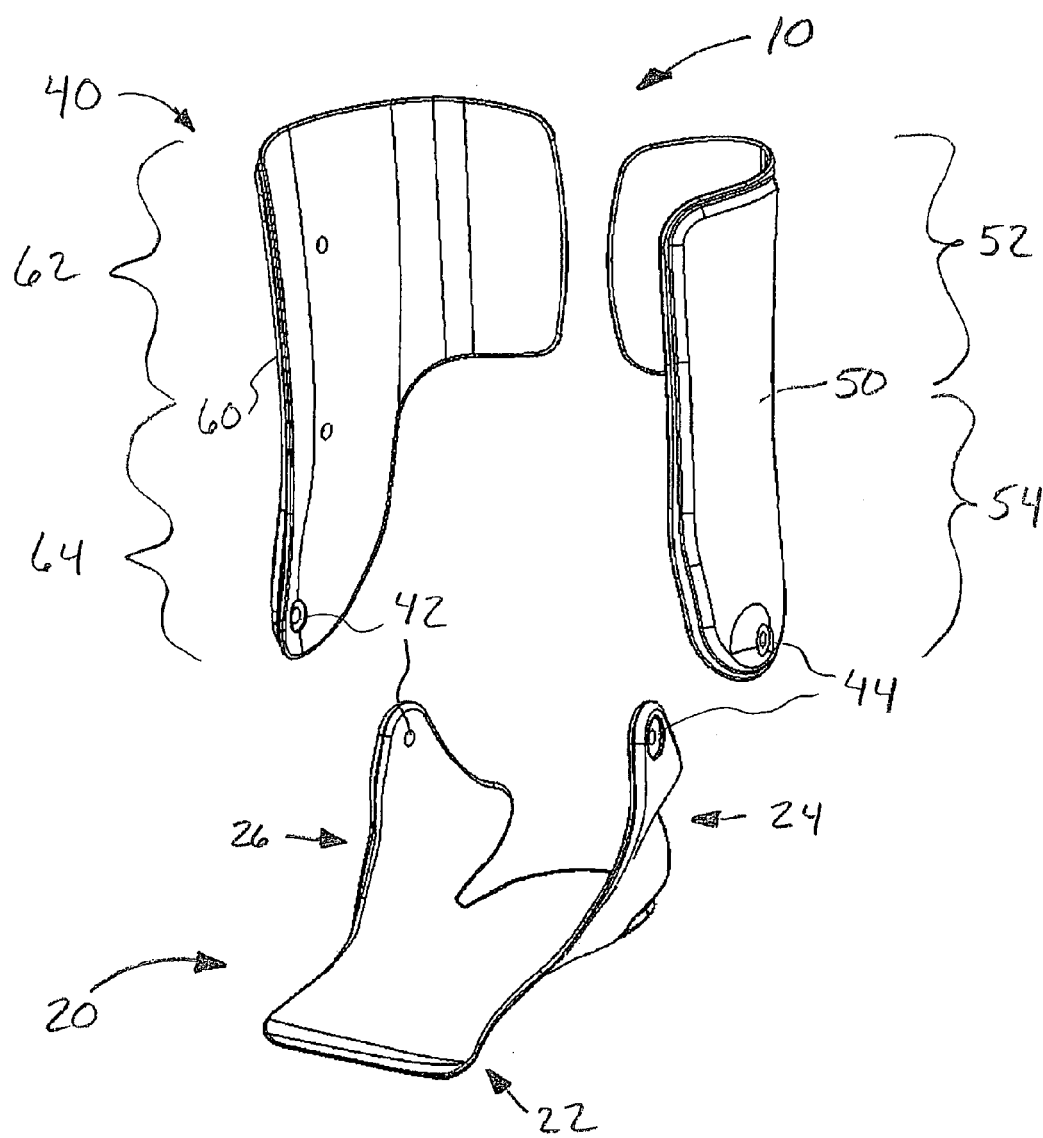
FIG. 13 is a front perspective exploded view of the foot plate and leg members of the ankle brace of FIG. 6.

Referring now also to FIG. 13 in the drawings, foot plate 20 and leg members 50 and 60 of ankle brace 10 are shown in a front perspective exploded view. Rearwardly extending medial flange 56 and rearwardly extending lateral flange 66 of upper portions 52 and 62 account for the shape of the soleus muscle by being adapted to overlap one another. Both lower portions 54 and 64 of medial leg member 50 and lateral leg member 60 extend outward to adapt to the outer edge of medial-upright portion 24 and lateral-upright portion 26. Lower portions 54 and 64 narrow in width and increase in thickness as they transition to adapt to asymmetric foot plate 20.

Pivot points 44 and 42 extend through medial leg member 50 and lateral-upright portion 26 as well as lateral leg member 60 and medial-upright portion 24. Rivets (not pictured) attach medial leg member 50 to lateral-upright portion 26 and lateral leg member 60 to medial-upright portion 24 through pivot points 44 and 42. Upper portions 52 and 62 of medial leg member 50 extend to approximately the same height as lateral leg member 60. Lateral leg member 60 extends lower than medial leg member 50 to account for the fibula's extending lower than the tibia.

Figure 14:
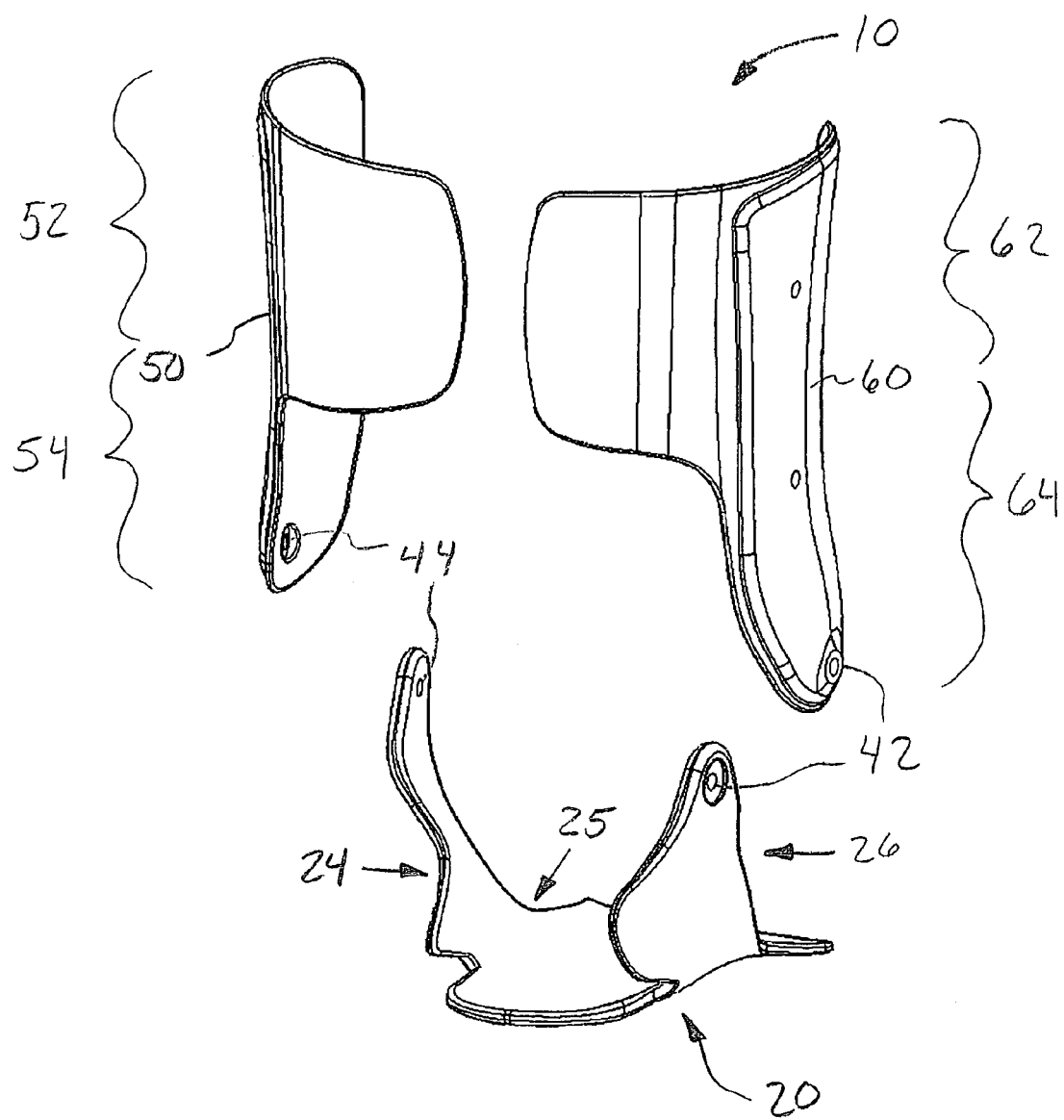
FIG. 14 is a rear perspective exploded view of the foot plate and leg members of the ankle brace of FIG. 6.

Referring now also to FIG. 14 in the drawings, foot plate 20 and leg members 50 and 60 of ankle brace 10 are shown in a rear perspective exploded view. Pivot points 44 and 42 are positioned slightly offset from one another to correspond to the anatomical relationship between the tibia and fibula. Rivets (not pictured) supply added rigidity to pivot points 44 and 42 connecting medial leg member 50 to medial-upright portion 24 and lateral leg member 60 to lateral-upright portion 26.

Medial leg member 50 attaches to medial-upright portion 24 of asymmetric foot plate 20 via pivot point 42. Lateral leg member 60 attaches to lateral-upright portion 26 of asymmetric foot plate 20 via pivot point 44. Pivot points 44 and 42 provide rotation of medial leg member 50 and lateral leg member 60 via rivets (not pictured) through asymmetric foot plate 20. Medial leg member 50 and lateral leg member 60 are shaped to mate with medial-upright portion 24 and lateral-upright portion 26 in order to allow the heel and Achilles tendon to articulate while secured by ankle stabilizing device 10. Medial leg member 50 and lateral leg member 60 are preferably made of a material that allows for some bending.

Because the fibula extends slightly below the tibia, the lateral malleolus and the medial malleolus direct the talus to bend slightly inward as the foot rotates relative to the lower leg. As the foot rotates to full extension, such that the top of the foot aligns substantially parallel to the front of the leg, the foot bends slightly inward relative to the position of the bottom of the foot.

Lateral leg member 60 remains slightly below medial leg member 50, as asymmetric foot plate 20 rotates. Accordingly, pivot points 44 and 42 act in concert with the upper portions of medial leg member 50 and lateral leg member 60 to allow uniform translation about asymmetric foot plate 20. The shape of medial leg member 50 and lateral leg member 60 constrain the range of rotation of asymmetric foot plate 20. The rear portions of medial leg member 50 and lateral leg member 60 can be concave to allow movement of the Achilles tendon and rotation of asymmetric foot plate 20. Asymmetric foot plate 20 may rotate so that the bottom of asymmetric foot plate 20 aligns substantially parallel with medial leg member 50 and lateral leg member 60 along both the reverse and forward positions.

Medial leg member 50 and lateral leg member 60 may rotate independent of one another when rearwardly extending medial flange 56 and rearwardly extending lateral flange 66 are not restrained to one another. Also both medial leg member 50 and lateral leg member 60 may laterally bend via lateral edge 27 and medial edge 25. Because lower portions 54 and 64 are thicker than upper portions 52 and 62, greater flexibility is provided to medial leg member 50 and lateral leg member 60 along upper portions 54 and 62.

As the calcaneus and talus bones articulate relative to the tibia and fibula, controlled motion is provided by ankle stabilizing device 10. As an ankle articulates, medial leg member 50, lateral leg member 60, and asymmetric foot plate 20 rotate via pivot points 44 and 42 to control the rotation of the wearer's ankle.

Figure 15:
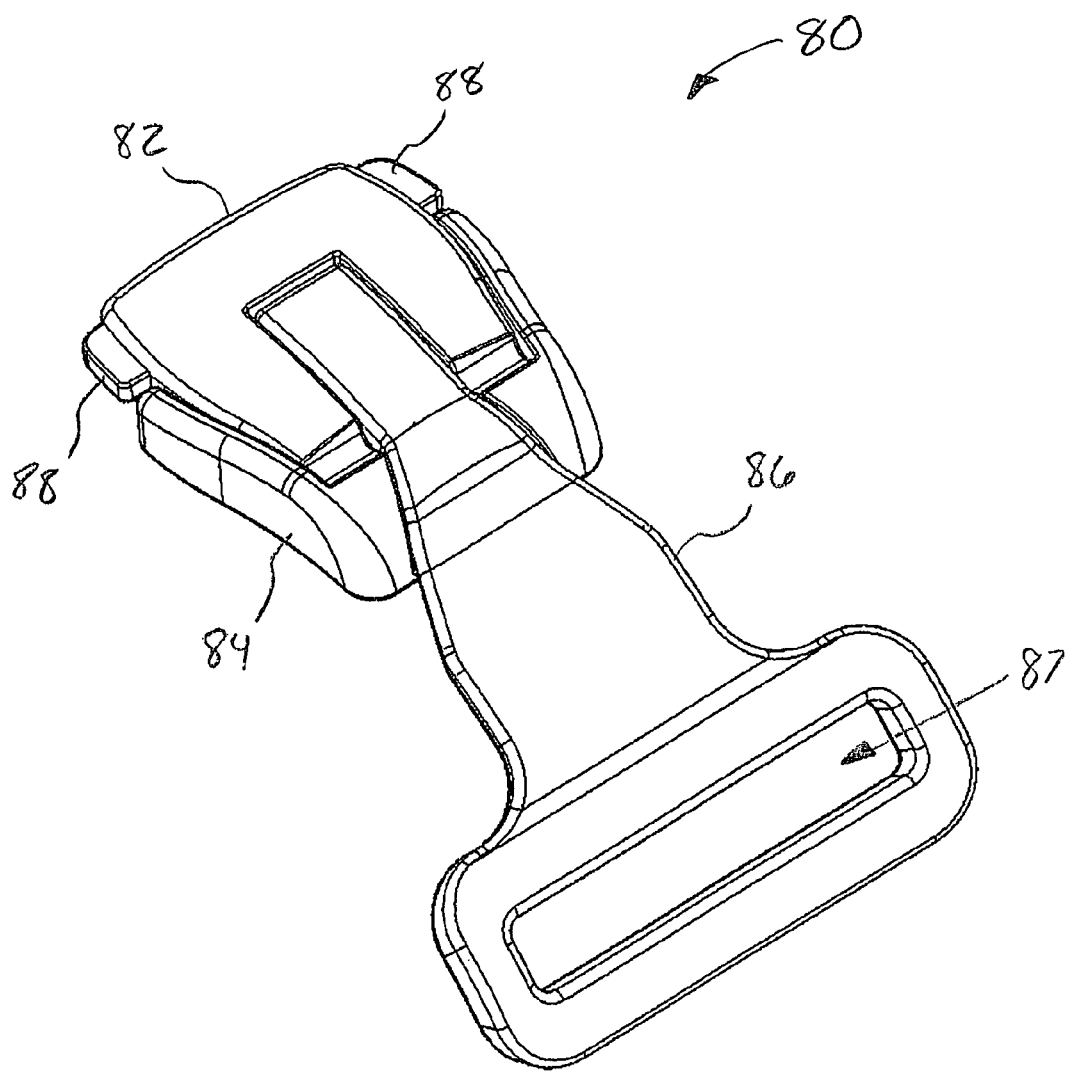
FIG. 15 is a perspective view of the latch buckle of the ankle brace of FIG. 6.

Referring now also to FIG. 15 in the drawings, a quick-release latch buckle 80 of ankle brace 10 is shown in a perspective view. Components of single pin quick release member 80 include tension lever 82, plate adapter 84, strap grasp 86, buttons 88, and rod 90.

Figure 16:
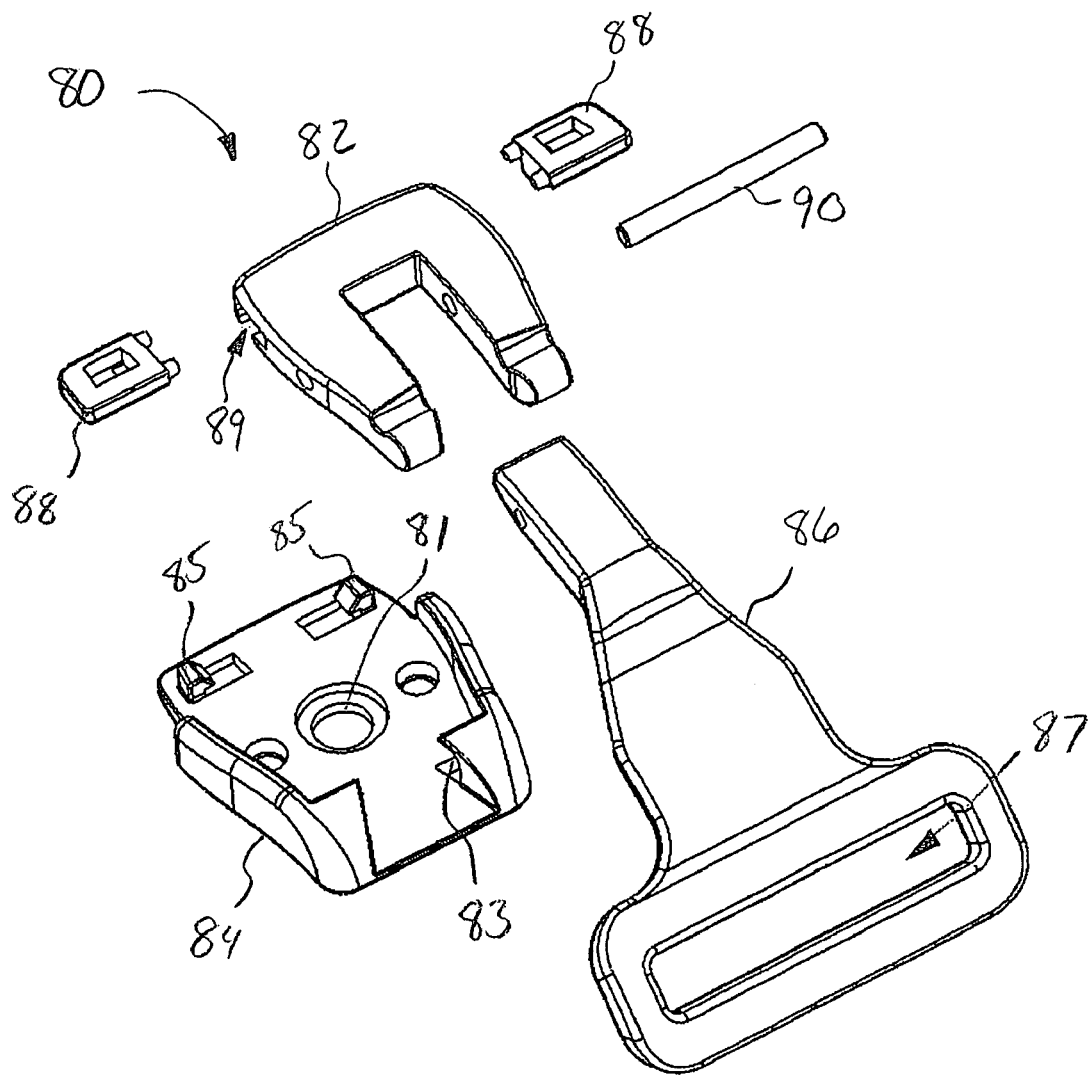
FIG. 16 is an exploded view of the latch buckle of FIG. 16.

Referring now also to FIG. 16 in the drawings, quick-release latch buckle 80 is shown in an exploded view. The front edge of tension lever 82 forms a hinge type adaptation 83 that mates with plate adapter 84. The hinge type adaptation 83 provides for pivoting of tension lever 82 about the front edge of plate adapter 84. Rod 90 extends through tension lever 82 and strap grasp 86 to provide for rotation of strap grasp 86 along tension lever 82. Strap grasp 86 provides an opening 87 for securing half strap member (shown in FIG. 1) and strap member (shown in FIG. 1).

A rivet (not shown) attaches plate adapter 84 via swivel point 81 to medial leg member 50. Swivel point 81 allows plate adapter 84 to swivel along the surface of medial leg member 50 or lateral leg member 60. Buttons 88 prevent the unintended release of tension lever 82 from plate adapter 84. Buttons 88 align within grooves 89 of tension lever 82 to engage notches 85 of plate adapter 84. Notches 85 are trapezoidally shaped and extend from the top of plate adapter 84 to provide for slip engagement of buttons 88. Additionally, each button 88 has two tapered pins extending outwardly on the side engaging notch 85. Two compression springs (not shown) center and engage on the tapered pins of both buttons 88, through two holes (not shown) in tension lever 82. These compression springs push buttons 88 away from tension lever 82 to maintain a latched condition. Buttons 88 must be simultaneously pressed to release tension lever 82 from plate adapter 84.

In operation, buttons 88 must be simultaneously pressed to allow tension lever 82 to pivot along the front edge of plate adapter 84. As tension lever 54 pivots, strap grasp 86 may rotate via rod 56, to grasp a first strap member 72 or a second strap member 74. A first strap member 72 or second strap member 74 may engage strap grasp 86 via opening 87. Once a first or second strap member is secured, tension lever 82, may be engaged to plate adapter 84. Buttons 88 engage notches 85 of plate adapter 84 via the slip connection provided via the trapezoidal shape. The spring loading of buttons 88 causes the buttons to press against notches 85 which secure tension lever 82 to plate adapter 84. As the tension lever is secured against plate adapter 84, strap grasp 86 rotates along rod 90 to pull half strap member or strap member in the direction of the tibular plate member or fibular plate member.

It is evident by the foregoing description that the invention of the subject application has significant benefits and advantages, including: (1) the heel support fits the shoe and the foot better, while providing increased support of the arch and midfoot; (2) the hinge pivot points more closely represent actual anatomical ankle pivot points; (3) the lower anterior half strap increases control of the syndesmosis to support acute or chronic upper ankle sprains, without putting pressure on the Achilles tendon; (4) the upper side shells are detachable from each other at the back, allowing adjustment of the circumference for a perfect fit on each patient; (5) the tough plastic alloy is heat-reformable at a relatively low temperature for custom fitting; (6) the quick-release latch buckles ease fitting and removal, increase life of straps, and feature dual release buttons to prevent accidental opening; and (7) the ankle brace is selectively tailored and configured to balance the stiffness and material alloy to slow movement of the ankle into inversion or eversion, where excessive strain would be placed on a user's ligaments.

The particular embodiments disclosed above are illustrative only, as the invention may be modified and practiced in different but equivalent manners apparent to those skilled in the art having the benefit of the teachings herein. It is therefore evident that the particular embodiments disclosed above may be altered or modified, and all such variations are considered within the scope and spirit of the invention. Accordingly, the protection sought herein is as set forth in the description. It is apparent that an invention with significant advantages has been described and illustrated. Although the present invention is shown in a limited number of forms, it is not limited to just these forms, but is amenable to various changes and modifications without departing from the spirit thereof.

What is claimed is:

1. An ankle brace, comprising:
   a base portion having a lateral edge and an opposing medial edge;
   a lateral upright portion extending upwardly from the lateral edge;
   a medial upright portion extending upwardly from the medial edge;
   a lateral leg member pivotally coupled to the lateral upright portion at a lateral pivot point;
   a medial leg member pivotally coupled to the medial upright portion at a medial pivot point;
   a lateral tab portion extending rearwardly from the lateral upright portion; and
   a medial tab portion extending rearwardly from the medial upright portion;
   wherein the lateral tab portion extends rearwardly so as to form a lateral void space below the lateral tab portion;
   wherein the medial tab portion extends rearwardly so as to form a medial void space below the medial tab portion; and
   a rear portion extending rearwardly from the base portion, the rear portion being configured so as to form the lateral void space between the rear portion and the lateral tab portion and configured to form the medial void portion between the rear portion and the medial tab portion.

2. The ankle brace according to claim 1, wherein a front portion of the base portion has a tapered front edge.

3. The ankle brace according to claim 2, wherein the front edge tapers downwardly.

4. The ankle brace according to claim 2, wherein the base portion is wider at the tapered front edge.

5. The ankle brace according to claim 1, wherein the base portion further comprises:
   a front portion;
   a rear portion; and
   an arch portion.

6. The ankle brace according to claim 5, wherein the arch portion forms an arcuate transition between the front portion and the rear portion.

7. The ankle brace according to claim 1, wherein the medial pivot point is higher than the lateral pivot point.

8. The ankle brace according to claim 1, wherein the lateral upright portion is anatomically contoured to conform to an outer side of a user's malleoli.

9. The ankle brace according to claim 1, wherein the medial upright portion is anatomically contoured to conform to an inner side of a user's malleoli.

10. The ankle brace according to claim 1, further comprising:
    a heel portion extending rearwardly from the base portion, the heel portion being concave upward.

11. The ankle brace according to claim 1, wherein the base portion is shaped to conform to the contours of a user's foot.

12. An ankle stabilizing device, comprising:
    a foot plate;
    a medial leg member having a longitudinal length, the medial leg member comprising:
        a lower medial portion;
        a medial tab portion extending rearwardly from the lower medial portion;
        an upper medial portion; and
        a medial flange extending rearwardly from the upper medial portion;
    a lateral leg member having a longitudinal length, the lateral leg member comprising:
        a lower lateral portion;
        a lateral tab portion extending rearwardly from the lower lateral portion;
        an upper lateral portion; and
        a lateral flange extending rearwardly from the upper lateral portion; and
    a rear portion extending rearwardly from the base portion, the rear portion being configured so as to form the lateral void space between the rear portion and the lateral tab portion and configured to form the medial void portion between the rear portion and the medial tab portion;
    wherein the medial leg member and the lateral leg member pivotally engage the foot plate; and
    wherein the longitudinal length of the medial leg is different from the longitudinal length of the lateral leg member.

13. The ankle stabilizing device according to claim 12, further comprising:
    an upper strap member for adjustably coupling the upper medial portion to the upper lateral portion, such that the upper medial portion and the upper lateral portion are compressed against a user's leg, the upper strap passing in front of and behind the user's leg.

14. The ankle stabilizing device according to claim 13, further comprising:
    a quick release member connected to the upper strap, the quick release member allowing the adjusted length of the upper strap to remain substantially constant during repeated administration of the ankle stabilizing device.

15. The ankle stabilizing device according to claim 12, further comprising:
    a lower strap member for adjustably coupling the lower medial portion to the lower lateral portion, such that the lower medial portion and the lower lateral portion are compressed against a user's leg, the lower strap passing only in front of the user's leg.

16. The ankle stabilizing device according to claim 15, further comprising:
    a quick release member connected to the lower strap, the quick release member allowing the adjusted length of the lower strap to remain substantially constant during repeated administration of the ankle stabilizing device.

17. The ankle stabilizing device according to claim 12, wherein the medial flange and the lateral flange are releasably coupled to each other.

18. The ankle stabilizing device according to claim 12, wherein both the medial flange and the lateral flange are releasably and adjustably coupled to each other.

19. The ankle stabilizing device according to claim 12, wherein the dimensions and the materials of the foot plate, the medial leg member, and the lateral leg member are selectively chosen, such that the stiffness of the ankle stabilizing device is tailored to slow down the inverting motion of an ankle joint enough to allow muscles of the ankle joint enough time to act to prevent spraining of the ankle joint.

* * * * *